US009761019B2

United States Patent
Yu et al.

(10) Patent No.: US 9,761,019 B2
(45) Date of Patent: Sep. 12, 2017

(54) COMPUTED TOMOGRAPHY USING SIMULTANEOUS IMAGE RECONSTRUCTION WITH MEASUREMENTS HAVING MULTIPLE DISTINCT SYSTEM MATRICES

(71) Applicant: TOSHIBA MEDICAL SYSTEMS CORPORATION, Otawara-shi (JP)

(72) Inventors: Zhou Yu, Palatine, IL (US); Yu Zou, Naperville, IL (US); Adam Petschke, Lake Bluff, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/592,662

(22) Filed: Jan. 8, 2015

(65) Prior Publication Data

US 2016/0203619 A1    Jul. 14, 2016

(51) Int. Cl.
*G06T 11/00*   (2006.01)
*A61B 6/03*    (2006.01)
(Continued)

(52) U.S. Cl.
CPC .......... *G06T 11/003* (2013.01); *A61B 6/032* (2013.01); *A61B 6/4241* (2013.01);
(Continued)

(58) Field of Classification Search
CPC ............ G06T 11/006; G06T 2211/421; G06T 11/003; G06T 2211/424; G06T 11/005;
(Continued)

(56) References Cited

U.S. PATENT DOCUMENTS 9,119,589 B2    9/2015 Zou
9,449,385 B2 *  9/2016 Petschke ............... G06T 7/0012
(Continued)

OTHER PUBLICATIONS

Jonathan Eckstein, "Augmented Lagrangian and Alternating Direction Methods for Convex Optimization: A Tutorial and Some Illustrative Computational Results" RUTCOR Research Report RRR 32-2012, Rutgers University, 2012, 35 Pages.
Sathish Ramani, et al., "A Splitting-Based Iterative Algorithm for Accelerated Statistical X-Ray CT Reconstruction" IEEE Trans Med Imaging, 2012, 31(3), 23 Pages.

*Primary Examiner* — Kenny Cese
(74) *Attorney, Agent, or Firm* — Oblon, McClelland, Maier & Neustadt, L.L.P.

(57) ABSTRACT

A method and apparatus is provided to reconstruct a collective image of a multiple method/geometry imaging system (e.g., a hybrid computed tomography system having energy-integrating detectors arranged in a third-generation geometry and photon-counting detectors arranged in a fourth generation geometry), wherein a splitting-based iterative algorithm using modified dual variables is used in the image reconstruction. Whereas a separate image for each method/geometry of the multiple method/geometry imaging system can be obtained by solving the distinct system-matrix equation corresponding to each respective method/geometry, the collective image is obtained by simultaneously solving a collective optimization problem including all respective system-matrix. The collective image is obtained more efficiently using variable splitting to subdivide the optimization into subproblems that are solved in an iterative fashion. For some applications, the collective image can be further improved by including a beam-hardening correction step.

20 Claims, 6 Drawing Sheets

(51) Int. Cl.
*A61B 6/00* (2006.01)
*A61B 6/06* (2006.01)

(52) U.S. Cl.
CPC ............ *A61B 6/4266* (2013.01); *A61B 6/482* (2013.01); *A61B 6/5205* (2013.01); *A61B 6/5258* (2013.01); *A61B 6/06* (2013.01); *A61B 6/4275* (2013.01)

(58) Field of Classification Search
CPC .......... G06T 2207/10081; A61B 6/032; A61B 6/4266; A61B 6/4241; A61B 6/482; A61B 6/5205; A61B 6/5258; A61B 6/06; A61B 6/4275
See application file for complete search history.

(56) References Cited

U.S. PATENT DOCUMENTS

| | | | |
|---|---|---|---|
| 2008/0019474 A1* | 1/2008 | Nakanishi ............... | A61B 6/032 378/9 |
| 2009/0122953 A1* | 5/2009 | Imai ....................... | A61B 6/032 378/5 |
| 2009/0161933 A1* | 6/2009 | Chen ....................... | G06T 11/006 382/131 |
| 2013/0343672 A1* | 12/2013 | Yu ........................... | G06T 11/003 382/276 |
| 2014/0226783 A1* | 8/2014 | Ning ....................... | A61B 6/032 378/5 |
| 2015/0146844 A1 | 5/2015 | Zamyatin et al. | |

* cited by examiner

COMPUTED TOMOGRAPHY USING SIMULTANEOUS IMAGE RECONSTRUCTION WITH MEASUREMENTS HAVING MULTIPLE DISTINCT SYSTEM MATRICES

BACKGROUND

Field

Embodiments described herein relate generally to a method of reconstructing computed tomography (CT) images, and more specifically to reconstructing CT images using projection data having multiple distinct system matrices geometries.

Description of the Related Art

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region (i.e., an X-ray projection plane) defining a cross-sectional slice of the body. At least one detector (and generally many more than one detector) on the opposite side of the body receives radiation transmitted through the body substantially in the projection plane. The attenuation of the radiation that has passed through the body is measured by processing electrical signals received from the detector.

Making projective measurements at a series of different projection angles through the body, a sinogram can be constructed from the projection data, with the spatial dimension of the detector array along one axis (e.g., the horizontal axis) and the time/angle dimension along the other axis (e.g., the vertical axis). The attenuation resulting from a particular volume with the body (e.g., a vertebra) will trace out a sine wave around the spatial dimension along the detector corresponding to the rotation axis of the CT system. Volumes of the body farther from the center of rotation correspond to sine waves with greater amplitudes than those corresponding to volumes nearer the center of rotation. The phase of each sine wave in the sinogram corresponds to the relative angular positions with respect to the rotation axis. Performing an inverse Radon transform (or an equivalent image reconstruction method) reconstructs an image from the projection data in the sinogram, where the reconstructed image corresponding to a cross-sectional slice of the body.

Conventionally, energy-integrating detectors have been used to measure CT projection data. Now, recent technological developments are making photon-counting detectors (PCDs) a feasible alternative to energy-integrating detectors. PCDs have many advantages including their capacity for performing spectral CT. To obtain the spectral nature of the transmitted X-ray data, the PCDs split the X-ray beam into its component energies or spectrum bins and count a number of photons in each of the bins. Since spectral CT involves the detection of transmitted X-rays at two or more energy levels, spectral CT generally includes dual-energy CT by definition.

Many clinical applications can benefit from spectral CT technology, which can provide improvement in material differentiation and beam-hardening correction. Further, semiconductor-based PCDs are a promising candidate for spectral CT, which is capable of providing better spectral information compared with conventional spectral CT technology (e.g., dual-source, kVp-switching, etc.).

One advantage of spectral CT, and spectral X-ray imaging in general, is that materials having atoms with different atomic number Z also have different spectral profiles for attenuation. Thus, by measuring the attenuation at multiple X-ray energies, materials can be distinguished based in the average spectral absorption profile of their constituent atoms (i.e., the effective Z of the material). Distinguishing materials in this manner (i.e., a high-Z material such as bone from a low-Z material such as water) enables a material decomposition from the spectral domain to the material domain. In some instances, this material decomposition is performed using a dual-energy analysis method.

The dual-energy analysis method can be used because the attenuation of X-rays in biological materials is dominated by two physical processes (i.e., photoelectric scattering and Compton scattering). Thus, the attenuation coefficient as a function of energy can be approximated by the decomposition $$\mu(E,x,y)=\mu_{PE}(E,x,y)+\mu_C(E,x,y),$$

where $\mu_{PE}(E,x,y)$ is the photoelectric attenuation and $\mu_C(E,x,y)$ is the Compton attenuation. This attenuation coefficient can be rearranged instead into a decomposition of a high-Z material (i.e., material 1) and a low-Z material (i.e., material 2) to become $$\mu(E,x,y)\approx\mu_1(E)c_1(x,y)+\mu_2(E)c_2(x,y),$$

where $c_1(x,y)$ and $c_2(x,y)$ are respectively spatial functions describing the concentrations of material 1 and material 2 located at positions (x,y).

Projection data in either the spectral domain or the material domain can be used for image reconstruction. Having obtained and corrected the projection data for measurement and detector artifacts, the projection data is prepared to reconstruct an image of an object OBJ. Generally, the image reconstruction problem can be solved using any of several methods including: back-projection methods (e.g., filtered back-projection), iterative reconstruction methods (e.g., the algebraic reconstruction technique (ART) method and the total variation minimization regularization methods), Fourier-transform-based methods (e.g., direct Fourier method), and statistical methods (e.g., maximum-likelihood expectation-maximization algorithm based methods).

Often the image reconstruction problem will be formulated as a matrix equation $$Af=g,$$

where g are the projection measurements of the X-rays transmitted through an object space that includes the object OBJ, A is the system matrix describing the discretized line integrals (i.e., the Radon transforms) of the X-rays through the object space, and $f$ is the image of object OBJ (i.e., the quantity to be solved for by solving the system matrix equation). The image $f$ is a map of the attenuation as a function of position.

One method of solving the system matrix equation is to recast it as an optimization problem. The optimization problem can also include a regularization term constraining the image solutions to adhere to known image characteristics (e.g., a body will generally have uniform attenuation densities within bodily organs and sharp changes in the attenuation density at the boundary of the organs, thus recommending a total variation minimization regularization term).

When the matrix equation is cast as an optimization problem, any of a number of iterative algorithms can be used to solve the optimization problem. For example, the algebraic reconstruction technique (ART) uses an iterative method of affine projections by refining estimates of the image $f$ through a succession of projections onto each of the affine spaces defined by the rows of the system matrix equation. Performing this series of affine projections and then repeating them again and again causes the image estimate to converge to a solution of the system matrix equation. Interjecting a regularization condition/term between series of affine projections imposes constraints on the solution, and ensures that the reconstructed image converges to a physically meaningful and realistic solution. For example, bodies are known to absorb radiation, making gain through a body (i.e., negative attenuation) an unphysical result. Therefore, a non-negative regularization condition can be imposed to eliminate unphysical gain regions in the reconstructed image.

Iterative reconstruction algorithms augmented with regularization conditions can produce high-quality reconstructions using only a few views even in the presence of significant noise. For few-view, limited-angle, and noisy projection scenarios, the application of regularization operators between reconstruction iterations seeks to tune the final result to be consistent with a certain a priori model. For example, enforcing positivity, as discussed above, is a simple but common regularization scheme.

A second regularization condition is total variation (TV) minimization in conjunction with projection on convex sets (POCS). The TV-minimization algorithm assumes that the image is predominantly uniform over large regions with sharp transitions at the boundaries of the uniform regions. When the a priori model corresponds well to the image object, these regularized iterative reconstruction algorithms can produce impressive images even though the reconstruction problem is significantly underdetermined (e.g., the few-view scenario), missing projection angles, or the data is noisy. The optimization problem with TV regularization can be expressed as $$\underset{u}{\operatorname{argmin}}\left\{\frac{1}{2}\|Af - g\|_2^2 + \lambda\|(|\nabla f|)\|_1\right\},$$

wherein the last term, the $l_1$-norm of the gradient-magnitude image, is the isotropic TV semi-norm. The spatial-vector image $\nabla u$ represents a discrete approximation to the image gradient. The expression $|\nabla f|$ is the gradient-magnitude image, an image array whose pixel values are the gradient magnitude at the pixel location.

Having formulated the optimization problem, there are many choices of algorithms for solving the optimization problem, some of which are more efficient than others, depending on the details of the optimization problem. For example, the dual-primal Chambolle-Pock (CP) algorithm can be efficient for solving certain image reconstruction optimization problems.

Two other related methods for iteratively solving optimization problems are the alternating direction method of multipliers (ADMM) and the augmented Lagrangian multiplier methods. These two methods are examples of splitting-based iterative algorithms. These splitting-based iterative methods exhibit the efficiencies introduced by subdividing a single optimization problem into a series of subproblems that can be solved in an iterative manner.

Although it can be developed in a slightly more general form, the following problem formulation is sufficient for most applications of the ADMM:

$$\min_{x \in \mathbb{R}^n} f(x) + g(Mx)$$

where, M is an m×n matrix, often assumed to have full column rank, and $f$ and g are convex functions on $\mathbb{R}^n$ and $\mathbb{R}^m$, respectively. In addition to values in, the functions $f$ and g can also have the value $+\infty$, so that constraints may be "embedded" in $f$ and g, in the sense that if $f(x)=\infty$ or $g(Mx)=\infty$, then the point x is considered to be infeasible.

By appropriate use of infinite values for $f$ or g, a very wide range of convex problems may be modeled by this optimization problem. To make the discussion more concrete, however, herein is described a simple illustrative example that fits very readily into this form without any use of infinite function values, and resembles in basic structure many of applications responsible for the resurgence of interest in the ADMM: the "lasso" or "compressed sensing" problem. This problem takes the form $$\min_{x \in \mathbb{R}^m} \frac{1}{2}\|Ax - b\|^2 + \nu\|x\|_1,$$

where A is a p×n matrix, b∈$\mathbb{R}^p$, and $\nu > 0$ is a given scalar parameter. The idea of the model is find an approximate solution to the linear equations Ax=b, but with a preference for making the solution vector x∈$\mathbb{R}^n$ sparse; the larger the value of the parameter $\nu$, the more the model prefers sparsity of the solution versus accuracy of solving Ax=b. While this model clearly has limitations in terms of finding sparse near-solutions to Ax=b, it serves as a good example application of the ADMM; many other now-popular applications have a similar general form, but may use more complicated norms in place $\|\cdot\|_1$; for example, in some applications, x is treated as a matrix, and one uses the nuclear norm (the sum of singular values) in the objective to try to induce x to have low rank.

Now, the classical augmented Lagrangian method and the ADMM are described for this optimization problem. First, note that the optimization problem can be rewritten, introducing an additional decision variable z∈$\mathbb{R}^m$ as min $f(x)+g(z)$ ST Mx=z The classical augmented Lagrangian algorithm, is described in the case of the above formulation by the recursions $$(x^{k+1}, z^{k+1}) \in \underset{x \in \mathbb{R}^n, z \in \mathbb{R}^m}{\operatorname{argmin}} \left\{ f(x) + g(z) + \langle \lambda^k, Mx - z \rangle + \frac{c_k}{2}\|Mx - z\|^2 \right\}$$

$$\lambda^{k+1} = \lambda^k + c_k(Mx^{k+1} - z^{k+1}).$$

where, $\{\lambda^k\}$ is a sequence of estimates of the Lagrange multipliers of the constraints Mx=z, while $\{(x^k, z^k)\}$ is a sequence of estimates of the solution vectors x and z, and $\{c_k\}$ is a sequence of positive scalar parameters bounded away from 0. The notation $\langle a, b \rangle$ denotes the usual Euclidean inner product $a^T b$.

In this setting, the standard augmented Lagrangian algorithm is not very attractive because the minimizations of $f$ and g in the second subproblem in the above expression are strongly coupled through the term $$\frac{c_k}{2}\|Mx-z\|^2,$$

and hence the subproblems are not likely to be easier to solve than the original problem. In contrast, the alternating direction method of multipliers (ADMM) is formulated into subproblems that are easier to solve. The ADMM problem takes the form $$x^{k+1} \in \operatorname*{argmin}_{x \in \mathbb{R}^n}\left\{f(x)+g(z^k)+\langle \lambda^k, Mx-z^k\rangle+\frac{c}{2}\|Mx-z^k\|^2\right\}$$

$$z^{k+1} \in \operatorname*{argmin}_{z \in \mathbb{R}^m}\left\{f(x^{k+1})+g(z)+\langle \lambda^k, Mx^{k+1}-z\rangle+\frac{c}{2}\|Mx^{k+1}-z\|^2\right\}$$

$$\lambda^{k+1} = \lambda^k + c(Mx^{k+1}-z^{k+1}).$$

Clearly, the constant terms $g(z^k)$ and $f(x^{k+1})$ as well as some other constants, may be dropped from the respective minimands in the above expressions. Unlike the classical augmented Lagrangian method, the ADMM essentially decouples the functions $f$ and g. In many situations, this decoupling makes it possible to exploit the individual structure of the $f$ and g so that the above expressions may be computed in an efficient and perhaps highly parallel manner.

The discussion thus far has centered on reconstructing a CT image for a single CT scanner system. A CT scanner system having multiple measurement methods/geometries can be treated identically to the single measurement method/geometry CT system by treating each measurement method and measurement geometry as a separate CT scanner system and reconstructing a separate image for each measurement method and measurement geometry. However, reconstructing separate images ignores the shared information among the multiple measurement methods/geometries that can be used to improve the image quality. Therefore, a better image reconstruction method will collectively process the projection data obtained using the multiple measurement methods/geometries to reconstruct a combined image.

BRIEF DESCRIPTION OF THE DRAWINGS

A more complete understanding of this disclosure is provided by reference to the following detailed description when considered in connection with the accompanying drawings, wherein.

DETAILED DESCRIPTION

There are many examples of imaging systems having multiple distinct measurement methods and/or measurement geometries. These measurements can be performed by a single imaging system integrating more than one measurement method/geometry, or these measurements can be performed by two imaging systems with the data being combined post acquisition for combined image reconstruction. As a third alternative, the same imaging system could make multiple separate scans/measurements of the same object but using different measurement configurations/modalities. Each of these alternatives has in common that the system matrix for image reconstruction will be different among the different measurement methods/geometries making image reconstruction using the conventional filtered back-projection method unsuitable.

Although it is possible to process measurements from each method/geometry separately to reconstruct separate images corresponding to each separate method and geometry, better image reconstruction is often obtained by reconstructing the images to reinforce the common features (e.g., spatial correlations) among the images or even to obtain a single combined image of all of the measurement methods and geometries.

For example, an imaging system could be a hybrid X-ray computed tomography CT imaging system including both energy-integrating detectors arranged in a third-generation geometry and also spectral photon-counting detectors (PCDs) sparsely arranged in a fourth-generation geometry— the energy-integrating detectors performing conventional (i.e., non-spectral) CT while the PCDs performed spectral CT on the polychromatic X-ray beam.

Whereas analytic methods exist (e.g., the filtered back-projection method) to perform the inverse Radon transform and reconstruct an image from data using a single measurement method/geometry, generally, there is no analytical solution for systems using multiple measurements methods/geometries. Fortunately, the image reconstruction problem for multi-method/geometry systems can be recast as an optimization problem in which a cost function involving all of the system matrices is minimized. Solutions of the hybrid third- and fourth-generation CT system using, among other methods, a weighted pseudo-inverse of the system matrix equations, has been considered in U.S. patent application Ser. No. 14/293,427, the contents of which are incorporated herein by reference in its entirety.

Unfortunately, the optimization problem can present challenges due to a slow rate of convergence arising from the fact that matrices used in the solution can be ill-conditioned. For example, when the noise in the data are correlated, the statistical weighting matrix becomes non-diagonal, and sometimes poorly conditioned, resulting in slow convergence of the optimization problem.

Although the discussion herein focuses on hybrid third- and fourth-generation systems, one of ordinary skill will recognize that the solution methods described herein are broadly applicable to solving any image reconstruction problem in which multiple distinct system matrices are to be solved collectively. Thus, the methods discussed herein are applicable to many multiple method/geometry imaging systems. The use of the hybrid third- and fourth-generation systems discussed herein is meant to be exemplary.

According to one embodiment, there is provided an apparatus for computed tomography (CT) image reconstruction using a plurality of datasets, each dataset corresponding to a respective detector configuration, and the apparatus includes processing circuitry. The processing circuitry is configured to obtain projection data representing an intensity of radiation detected at a plurality of detectors, the radiation having been transmitted through an object space, wherein the projection data includes a plurality of datasets, and each dataset corresponds to a respective detector configuration of a plurality of detector configurations. The processing circuitry is also configured to reconstruct a combined image using the plurality of datasets, wherein the combined image is reconstructed using at least one modified-dual variable and using a splitting-based subproblem method.

According to one aspect of the apparatus, the processing circuitry is further configured to reconstruct the combined image using the splitting-based subproblem method that is a sinogram subproblem method. The sinogram subproblem method includes that the processing circuitry is configured to update a plurality of approximate sinograms, each approximate sinogram corresponding to a respective dataset of the projection data, wherein each respective approximate sinogram is calculated to minimize a corresponding sinogram-update expression using a corresponding previous approximate-combined image and a corresponding previous plurality of modified-dual variables. Further, the sinogram subproblem method includes that the processing circuitry is configured to update an approximate-combined image, wherein the approximate-combined image is calculated to minimize a combined-image-update expression using the updated plurality of approximate sinograms and the previous plurality of modified-dual variables. In addition, the sinogram subproblem method includes that the processing circuitry is configured to update the plurality of modified-dual variables using a plurality of modified-dual-variable-update expressions, wherein each modified-dual-variable-update expression updates the corresponding modified-dual variable using the corresponding previous plurality of modified-dual variables, the corresponding updated approximate sinogram and the updated approximate-combined image.

According to one aspect of the apparatus, the processing circuitry is further configured to reconstruct the combined image using the splitting-based subproblem method that is an image subproblem method. The image subproblem method includes that the processing circuitry is configured to update a plurality of separate images using a plurality of separate-image-update expressions, each separate image corresponding to a respective dataset of the projection data, wherein each respective separate image is calculated to optimize a corresponding separate-image-update expression using a previous plurality of separate images and a previous at least one modified-dual variable. Further, the image subproblem method includes that the processing circuitry is configured to update the at least one modified-dual variable using an updated plurality of separate images and the previous at least one modified-dual variable.

According to another embodiment is provided a CT imaging apparatus that includes a radiation source configured to provide radiation into an object space. The CT imaging apparatus also includes a plurality of detectors configured to detect radiation exiting the object space. Also included in the CT imaging apparatus is a rotation component provided around the object space and configured to rotate around the object space, wherein the radiation source is fixedly connected to the rotation component. In addition, the CT imaging apparatus includes processing circuitry. The processing circuitry is configured to obtain projection data representing an intensity of radiation transmitted through the object space and detected at the plurality of detectors, the projection data including a plurality of datasets, wherein each dataset corresponds to a respective detector configuration of a plurality of detector configurations. Also, the processing circuitry is configured to reconstruct the combined image using the plurality of datasets, wherein the combined image is reconstructed using at least one modified-dual variable and using a splitting-based subproblem method.

According to another embodiment is provided a CT image reconstruction method. The method includes obtaining projection data representing an intensity of radiation transmitted through an object space and detected at a plurality of detectors, the projection data including a plurality of datasets, wherein each dataset corresponds to a respective detector configuration of a plurality of detector configurations. Also, the method includes reconstructing the combined image using the plurality of datasets, wherein the combined image is reconstructed using at least one modified-dual variable and using a splitting-based subproblem method.

Figure 1:
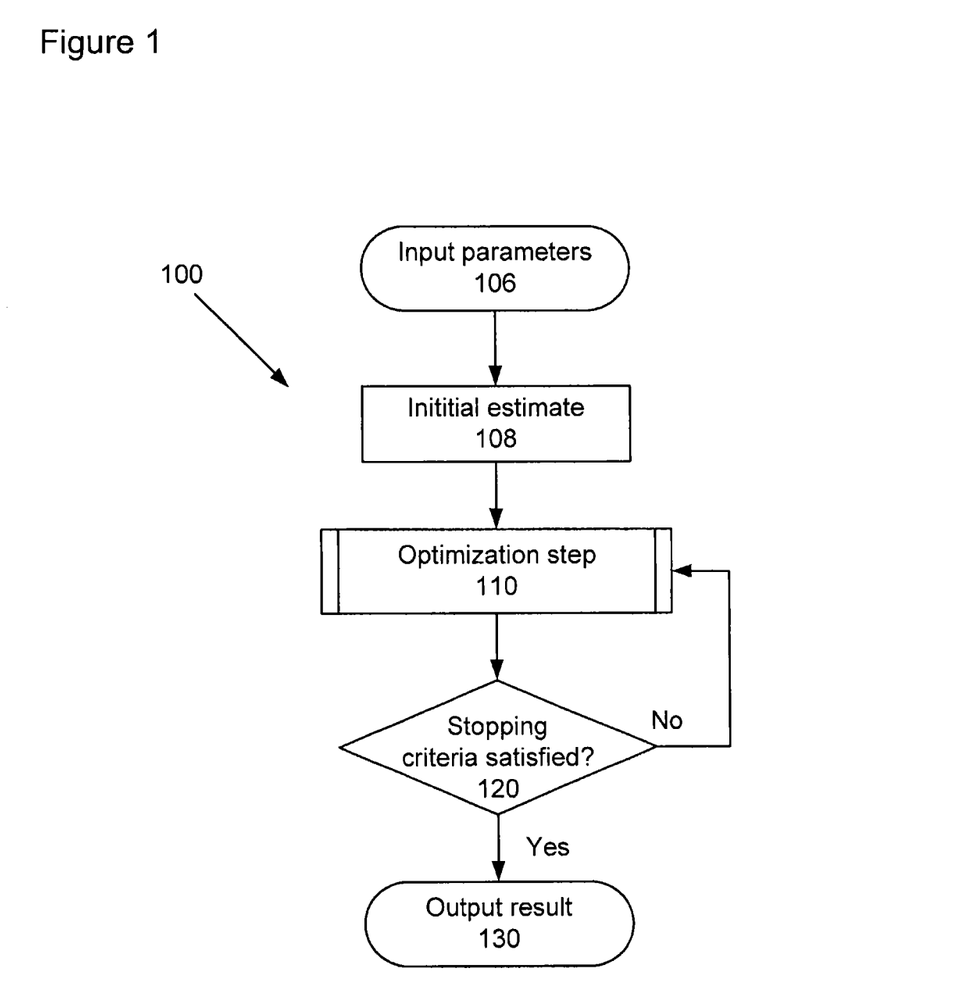
FIG. 1 shows a flow diagram of an implementation of an image reconstruction method.

Referring now to the drawings, wherein like reference numerals designate identical or corresponding parts throughout the several views, FIG. 1 shows a method 100 to reconstruct an image using a multiple method/geometry imaging system, such as the hybrid third- and fourth-generation system discussed in U.S. patent application Ser. No. 14/293,427.

First, the method 100 gathers the input data (e.g., the projection data which may have been previously corrected for detector response and measurement artifacts) at input 106.

Next, at step 108, an initial estimate is obtained for the reconstructed image. In one implementation, the initial estimate is obtained by performing separately the image reconstruction on each type of projection data (i.e., a separate image for each measurement method and/or measurement geometry), and the initial estimate is then a combination image derived from combining together each of the separate images. For example, the process of combining together each of the separate images can be performed by averaging together all of the separate images.

After step 108, method 100 proceeds to process 110, wherein an optimization step is performed. In one implementation, the image reconstruction problem can be recast into a cost function minimization problem, wherein the cost function is expressed as $$C(f) = \|g_1 - A_1 f\|_{W_1}^2 + \|g_2 - A_2 f\|_{W_2}^2 + \beta U(x),$$

wherein $g_1 = A_1 f$ is the system matrix equation for the first measurement method/geometry, $g_2 = A_2 f$ is the system matrix equation for the second measurement method/geometry, and $\beta U(x)$ is a regularization term. The notation $\|x\|_W^2$ signifies a weighted inner product of the form $x^T W x$. The choice of regularization term can be based on the details of the imaging problem. The regularization term can be one of a negative absorption constraint, quadratic regularization, edge-preserving regularization, such as Gaussian Markov Random Field regularization, a total-variation minimization regularization, and a vectorial total-variation minimization regularization.

The cost-function minimization problem can be solved using a single-step constrained optimization $$(\tilde{g}_1, \tilde{g}_2, f) = \underset{\tilde{g}_1 = A_1 f, \tilde{g}_2 = A_2 f}{\mathrm{argmin}} \left\{ \|g_1 - \tilde{g}_1\|_{W_1}^2 + \|g_2 - \tilde{g}_2\|_{W_2}^2 + \beta U(f) \right\}.$$

Using standard iterative methods such as ordered subsets algorithms based on separable quadratic surrogates, and conjugate gradient methods to solve this unconstrained optimization problem can result in slow convergence due to the non-diagonal statistical weighting matrices $W_1$ and $W_2$ not being diagonal and due to the poor condition of $W_1$ and large dynamic range of $W_2$, making the problem ill-conditioned.

By replacing the non-diagonal statistical matrices with the diagonal matrix, the optimization problem is converted from a maximum-likelihood problem to a least-squares problem. In exchange for giving up the better image quality of the maximum a posteriori (MAP) solution, the least-squares formulation will normally converge faster than the MAP formulation when using the conventional iterative optimization methods discussed above. However, herein the focus is on solving the MAP formulation, which uses the non-diagonal statistical weighting matrices. Therefore, methods that solve the maximum-likelihood problem, but also have a faster convergence rate are desired.

The single-step constrained optimization problem above can also be solved by recasting the problem as an unconstrained problem using augmented Lagrangian method $$(\tilde{g}_1, \tilde{g}_2, f) = \operatorname{argmin}\{\|g_1 - \tilde{g}_1\|^2_{W_1} + \|g_2 - \tilde{g}_2\|^2_{W_2} + \beta U(f) + \ldots \|\tilde{g}_1 - A_1 f - \eta_1\|^2_{D_1} + \|\tilde{g}_2 - A_2 f - \eta_2\|^2_{D_2}\},$$

wherein $D_1$ and $D_2$ are arbitrary diagonal matrices chosen to improve the condition number of the problem, and $\eta_1$ and $\eta_2$ are modified-dual variables, that has a closed form update equation.

Figure 2:
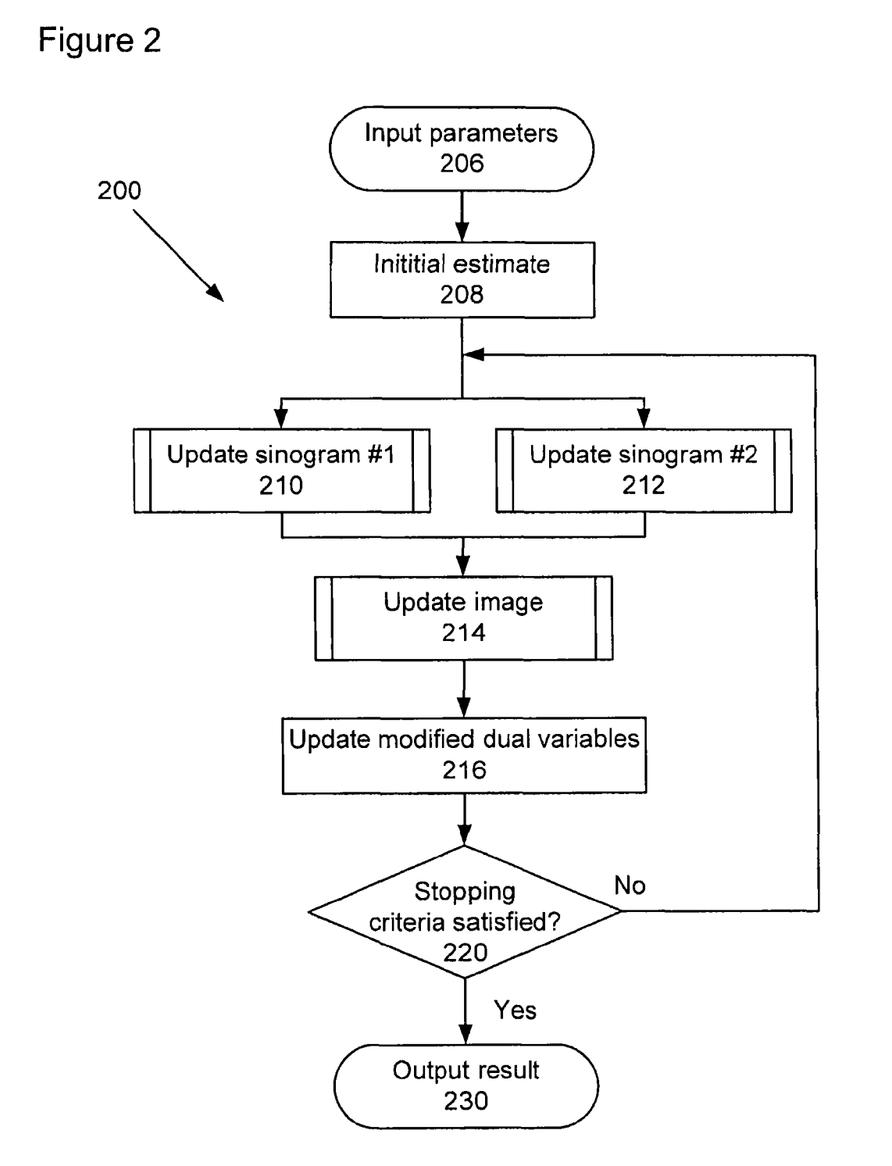
FIG. 2 shows a flow diagram of an implementation of a sinogram-splitting image reconstruction method.
Figure 3:
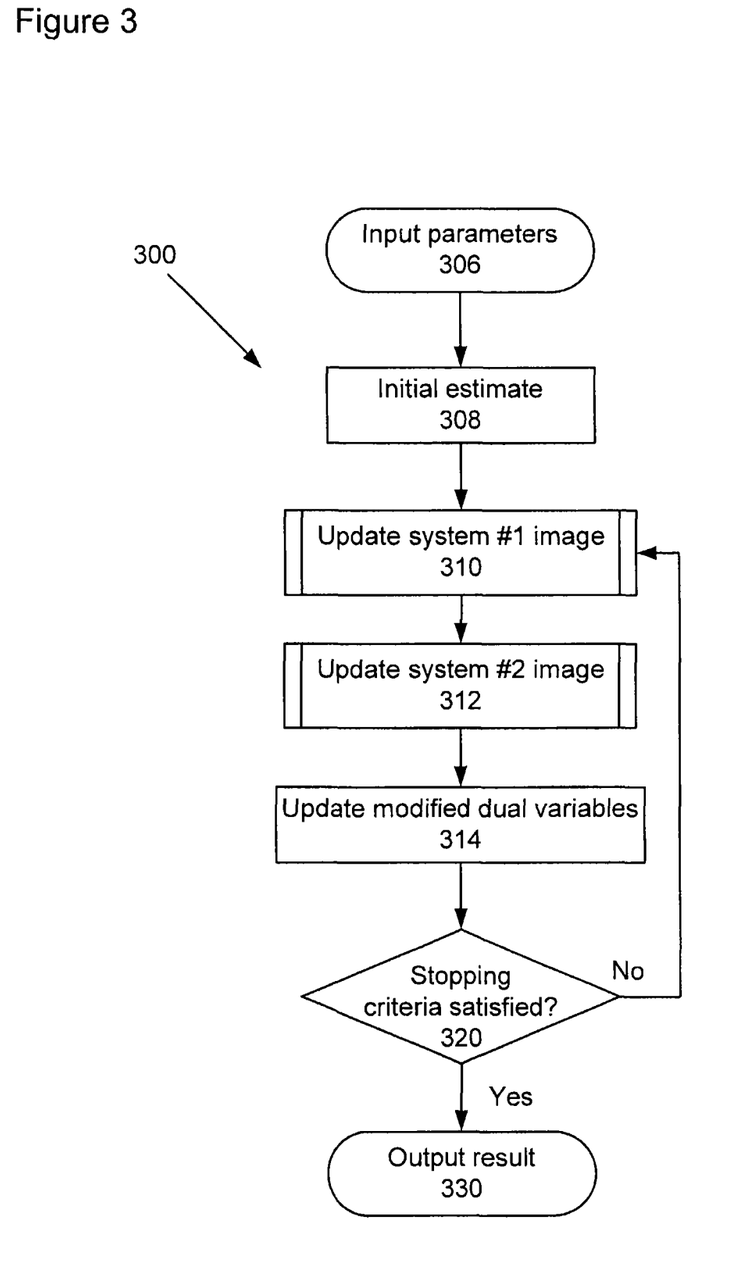
FIG. 3 shows a flow diagram of an implementation of an image-splitting image reconstruction method.
Figure 4:
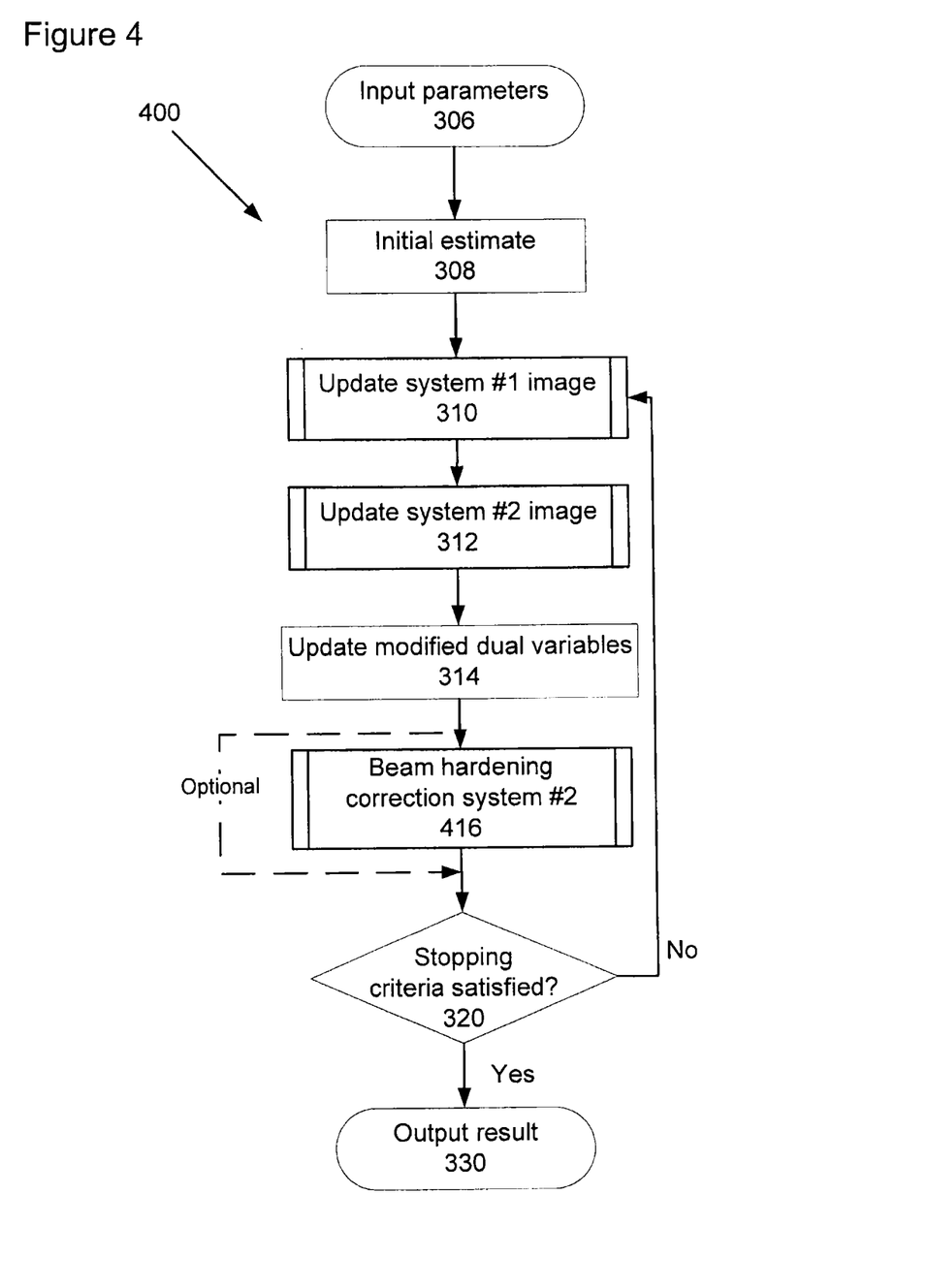
FIG. 4 shows a flow diagram of an implementation of an image-splitting image reconstruction method having a beam-hardening correction step.

Both the single-step constrained optimization problem and single-step unconstrained optimization problem for the multiple method/geometry imaging system are not splitting-based methods because they do not split the optimization problem into sub-parts, but instead maintain the optimization problem as a single step. In contrast, FIGS. 2, 3, and 4 illustrate splitting-based methods wherein the optimization problem is subdivided into sub-problems.

In addition to whether the optimization problem is cast as a constrained or unconstrained problem, the details of the optimization step depend on the choice of optimization algorithm—the choices including: iterative coordinate descent methods, block-based coordinate descent, ordered subsets algorithms based on separable quadratic surrogates, the (preconditioned) nonlinear conjugate gradient method, gradient descent methods, the (M)FISTA algorithm, and split-Bergman-type schemes.

Having completed an optimization step at process 110, method 100 proceeds to the inquiry at step 120, wherein method 100 evaluates whether the stopping criteria have been satisfied. The stopping criteria can include conditions on the convergence of the image $f$ and related values $g_1$ and $g_2$, as well as conditions on the number of iterations/operations performed. For example, the stopping criteria can be satisfied when either the value of a difference measure between the current $f^{n+1}$ and previous $f^n$ values of the image fall below a predefined threshold $\epsilon$, or the number of loop iterations n reaches a predefined value $n_{max}$. If the stopping criteria are satisfied, then the method 100 proceeds to step 130, wherein the results are output. Otherwise, the loop continues by proceeding from inquiry 120 back to the optimization step at process 110.

The non-diagonal statistical weighted optimization problem can be solved more efficiently by further splitting the problem into subproblems, similar to how the alternating direction method of multipliers (ADMM) solution resembles a further splitting into subproblems of the augmented Lagrangian multiplier problem. This concept is based on the principle of variable splitting. Variable splitting is a method that decomposes a complicated problem into subproblems by introducing auxiliary variables and constraints. The subproblems are relatively easy to solve compared to the original problem, therefore the computational cost can be reduced. Conventionally, variable splitting has been applied to solve iterative tomographic reconstruction problems by separating the data fidelity and regularization terms. Herein, auxiliary variables are introduced to decompose the original problem into sub-problems corresponding to each measurement method/geometry.

Details of the augmented Lagrangian method and the ADMM methods can be found in J. Eckstein, "Augmented Lagrangian and Alternating Direction Methods for Convex Optimization: A Tutorial and Some Illustrative Computational Results" RUTCOR Research Report RRR 32-2012, Rutgers University, December 2012, incorporated herein by reference in its entirety. Additional information on conventional variable splitting-based iterative algorithms can be found in A. Ramani and J. Fessler, "A splitting-based iterative algorithm for accelerated statistical X-ray CT reconstruction", IEEE Trans. Med. Imaging, 31, p. 577 (2012), incorporated herein by reference in its entirety.

FIG. 2 shows a method 200 of image reconstruction for a two method/geometry imaging system. Similar to method 100, this method starts with the steps of inputting parameters at step 206, and obtaining initial estimates at step 208. Process 210 solves the optimization problem $$\tilde{g}_1^{(n+1)} = \operatorname*{argmin}_{\tilde{g}_1}\{\|g_1 - \tilde{g}_1\|^2_{W_1} + \|\tilde{g}_1 - A_1 f^{(n)} - \eta_1^{(n)}\|^2_{D_1}\},$$

while the process 212 solves the optimization problem $$\tilde{g}_2^{(n+1)} = \operatorname*{argmin}_{\tilde{g}_2}\{\|g_2 - \tilde{g}_2\|^2_{W_2} + \|\tilde{g}_2 - A_2 f^{(n)} - \eta_2^{(n)}\|^2_{D_2}\}.$$

These two sinogram update problems can be solved in parallel and are straightforward to solve efficiently using a ray-by-ray method. In one implementation, the sinogram update equations are solved using the matrix solutions $$\tilde{g}_1^{(n+1)} = (W_1 + D_1)^{-1}(W_1 g_1 + D_1(A_1 x^{(n)} + \eta_1^{(n)})), \text{ and}$$

$$\tilde{g}_2^{(n+1)} = (W_2 + D_2)^{-1}(W_2 g_2 + D_2(A_2 x^{(n)} + \eta_2^{(n)})).$$

Following processes 210 and 212, the method 200 proceeds to process 214, wherein the image is updated according to the optimization problem $$(f^{(n+1)}) = \operatorname*{argmin}_{f}\{\beta U(f) + \|\tilde{g}_1^{(n+1)} - A_1 f - \eta_1^{(n)}\|^2_{D_1} + \|\tilde{g}_2^{(n+1)} - A_2 f - \eta_2^{(n)}\|^2_{D_2}\}.$$

A significant advantage of this optimization problem over previous formulations is that non-diagonal statistical weighting matrices are not used. Rather than using non-diagonal statistical weighting matrices, diagonal matrices $D_1$ and $D_2$ are used in the inner product normalizations $\|\cdot\|_D^2$.

There are several methods of solving the image optimization problem in the update image process 214. In one implementation, a gradient descent method is used to converge towards an optimal image. In another implementation, a variation of the algebraic reconstruction technique method with a regularization term can be used to iterate towards an optimal image.

In one implementation, the convergence criteria of the method for solving the image optimization problem in process 214 will depend on the value of the large iteration loop variable. The large iteration loop is the iterative process including each of the steps and processes 210 through 220. In contrast, each of the optimization subproblems contained in processes 210, 212, and 214 can be solved, in certain implementations, using iterative methods, wherein the iterative methods will each include a small iterative loop and a small iteration loop variable. Referring to iterative loops, the terms "small" and "large" denote whether the iterative loop is internal to one of processes 210, 212, and 214 (i.e., a small iterative loop) or is an iterative loop involving multiple steps in the method (i.e., the loop involving steps and process 210 through 220 is a large iterative loop).

Because, in certain implementations, the sinogram variables $\tilde{g}_1^{(n)}$ and $\tilde{g}_2^{(n)}$ and the image variable $\tilde{f}^{(n)}$ can change significantly between iterations, especially in early iterations of the large loop, resources are more efficiently used by reducing the number of small-loop iterations in process 214 (i.e., not carrying the optimization process all the way to convergence) especially during early iterations of the large loop. This can be achieved, in the small iterative loop in process 214, by using relaxed convergence criteria and/or by using a small number for the maximum number of iterations.

In one implementation, the stopping criteria of the small iterative loop corresponding to process 214 is that the small loop stops when the small loop reaches a predetermined small number of iterations independent of the value of the large-loop iteration variable. In another implementation, the stopping criteria of the small loop within process 214 will be conditioned on the large-loop iteration number, wherein the small loop will stop after a predetermined small number of iterations when the large-loop iteration variable is small, and the small loop will stop after a predetermined larger number of iterations when the large-loop iteration variable is not small.

In one implementation, a filtered back-projection method will be used to solve each system matrix equation separately, and then the two separate image solutions will be blended together by, e.g., averaging the two images.

In one implementation, a preconditioner matrix approximating $$(\lambda_1 A_1^T D_1 A_1 + \lambda_2 A_2^T D_2 A_2 + \beta U)^{-1}$$

is used to precondition the image optimization expression in order to accelerate convergence.

Having updated the image $f^{(n+1)}$, the next step in method 200 is step 216, wherein the modified-dual variables $\eta_1$ and $\eta_2$ are updated according to $$\eta_1^{(n+1)} = \eta_1^{(n)} + (\tilde{g}_1^{(n+1)} - A_1 x^{(n+1)}), \text{ and}$$

$$\eta_2^{(n+1)} = \eta_2^{(n)} + (\tilde{g}_2^{(n+1)} - A_2 x^{(n+1)}).$$

Having updated the modified-dual variables, the method 200 proceeds to inquiry 220. Similar to step 120 of method 100, step 220 inquires whether the stopping criteria is satisfied. The stopping criteria can include conditions on the convergence of the image $f$ and on the convergence of the values $g_1$ and $g_2$. Additionally, the stopping criteria can include conditions on the number of iterations/operations performed. For example, the stopping criteria can be satisfied when either the value of a difference measure between the current $f^{(n+1)}$ and previous $f^{(n)}$ values of the image fall below a predefined threshold $\epsilon$ or the number of loop iterations n reaches a predefined value $n_{max}$. If the stopping criteria are satisfied, then the method 200 proceeds to step 230, wherein the results are output. Otherwise, the loop begins another iteration by proceeding from inquiry 220 back to the update sinogram steps at processes 210 and 212.

FIG. 3 shows a flow diagram of a method 300 for the image reconstruction of a two-method/geometry imaging system. Similar to method 100 and method 200, this method starts with the steps of imputing parameters, at step 306, and obtaining initial estimates at step 308. Also similar to method 200, method 300 splits the optimization problem into multiple subproblems. Method 300 solves for two images, wherein one image corresponds to the first method/geometry of the CT system and a second image corresponds to the second method/geometry of the CT system. Process 310 of method 300 updates a first image, corresponding to the first method/geometry, using the update expression $$f^{(n+1)} = \arg\min_f \left\{ \beta U(f) + \|g_1 - A_1 f\|_{W_1}^2 + \lambda \left\| f - \tilde{f}^{(n)} - \eta^{(n)} \right\|^2 \right\}.$$

Similarly, process 312 of method 300 updates a second image, corresponding to the first measurement method/geometry, using the update expression $$\tilde{f}^{(n+1)} = \arg\min_{\tilde{f}} \left\{ \|g_2 - A_2 \tilde{f}\|_{W_2}^2 + \lambda \left\| f^{(n)} - \tilde{f} - \eta^{(n)} \right\|^2 \right\}.$$

There are many methods that can be used to solve the optimization problems in processes 310 and 312. These optimization methods include conventional local and global search optimization methods (e.g., gradient descent methods, stochastic search methods, etc.). Additionally, an ART method can be used to iterate towards an optimal image.

In one implementation, rather than solving a matrix equation, a filtered back-projection method is used to solve the system matrix equations in each of process 310 and 312. Thus, separate images are obtained for each of the first measurement method/geometry and the second measurement method/geometry. Then, after obtaining separate images for each distinct measurement method/geometry, the separate images are blended together to obtain a combined image.

In another implementation, when an iterative method is used internally to update the images in processes 310 and 312, then the smaller loops (i.e., the loops internal to each of processes 310 and 312) are only carried through a small number of iterations during each iteration of the larger loop (i.e., the loop including all of the steps and processes in 310 through 320). This limited number of small-loop iterations is especially significant during early iterations of the large loop when the updated images $f^{(n+1)}$ and $\tilde{f}^{(n+1)}$ are undergoing significant changes during each large-loop iteration.

Having completed the image updates in processes 310 and 312, the method 300 proceeds to update the modified-dual variables in step 320 according to the expression $$\eta^{(n+1)} = \eta^{(n+1)} + (f^{(n+1)} - \tilde{f}^{(n+1)}).$$

Having updated the modified-dual variables, the method 300 proceeds to inquiry 320. Similar to step 120 of method 100 and step 220 of method 200, step 320 inquires whether the stopping criteria is satisfied. The stopping criteria can include conditions on the convergence of the images $f^{(n+1)}$ and $\tilde{f}^{(n+1)}$, as well as conditions on the number of iterations/operations performed. For example, the stopping criteria can be that when the value of a difference measure between the current values $f^{(n+1)}$ and $\tilde{f}^{(n+1)}$ and the previous values $f^{(n)}$ and $\tilde{f}^{(n)}$ of the image fall below a predefined threshold $\epsilon$ or the number of loop iterations n reaches a predefined value $n_{max}$, then the stopping criteria are satisfied. If the stopping criteria are satisfied, then the method 300 proceeds to step 330, wherein the results are output. Otherwise, the loop continues by proceeding from inquiry 220 back to the update first image steps at 310.

FIG. 4 shows a flow diagram of method 400, which is a variation of method 300. The primary difference between method 400 and method 300 is the addition of step 416. Method 400 is applicable when the system #2 image suffers from beam-hardening artifacts and the system #1 image provides information that can be used to perform beam-hardening corrections on the system #2 projection data $g_2$, as is the case where system #2 uses energy-integrating detectors and system #1 uses spectrally resolving detectors (e.g., photon-counting detectors).

In step 416, a beam-hardening correction is applied to the projection data $g_2$ of the second measurement method/geometry system. The optional line-circumventing step 416 indicates that although the beam-hardening correction is beneficial to improve the image quality, most of the benefits of the beam-hardening correction can be achieved without performing this correction on each large-loop iteration. Thus, this correction can be omitted during some large-loop iterations provided the correction is performed periodically throughout the large-loop iterations.

The beam-hardening correction results in a change to the second system projection data $g_2$. As discussed in U.S. patent application Ser. No. 14/293,427, the beam-hardening correction for each value of the projection data using a measurement method/geometry of energy-integrating detectors arranged in a third-generation geometry is calculated as $$BHC(l) = \ln \int dES_{3rd}(E) \exp[-L_1^{(3rd)}(l)\Delta\mu_1(E,l) - L_2^{(3rd)}(l)\Delta\mu_2(E,l)],$$

wherein $S_{3rd}(E)$ is the detected energy spectrum by the energy-integrating detector in the absence of an absorbing image object OBJ (i.e., when the image object OBJ is air), $L_1^{(3rd)}$ and $L_2^{(3rd)}$ are the respective projection lengths of a first and second material along the integration path l, corresponding to the trajectory of the X-rays incident on the energy-integrating detector. The deviations about the mean absorption coefficients are given by $$\Delta\mu_1(E,l) = \mu_1(E) - \bar{\mu}_1(l) \text{ and}$$

$$\Delta\mu_2(E,l) = \mu_2(E) - \bar{\mu}_2(l),$$

wherein the mean absorption coefficients are given by $$\bar{\mu}_1(l) = \int dES_{3rd}(E,l)\mu_1(E) \text{ and}$$

$$\bar{\mu}_2(l) = \int dES_{3rd}(E,l)\mu_2(E).$$

The l in $S_{3rd}(E,l)$ reflects the fact that the energy spectra can be different for different ray trajectories in the X-ray beam. The projection values for system #2 are each given by $$g_2(l) = -\ln \int dES_{3rd}(E) e^{-L_1^{(3rd)}\mu_1(E) - L_2^{(3rd)}\mu_2(E)}$$

$$= L_1^{(3rd)}(l)\bar{\mu}_1(l) + L_2^{(3rd)}(l)\bar{\mu}_2(l) -$$

$$\ln \int dES_{3rd}(E) e^{-L_1^{(3rd)}\Delta\mu_1(E,l) - L_2^{(3rd)}\Delta\mu_2(E,l)}$$

$$= L_1^{(3rd)}(l)\bar{\mu}_1(l) + L_2^{(3rd)}(l)\bar{\mu}_2(l) - BHC(l)$$

Therefore, the projection values can be corrected for beam hardening using, in step 416, the correction $$g_2^{(Corr)}(l) = g_2(l) + BHC(l).$$

In one implementation, this beam-hardening correction is performed each time the loop iteration variable n is exactly divisible by the integer given by $n_{BHC}$. Otherwise, the beam-hardening correction is omitted from the large loop. For example, if the beam-hardening correction is performed one time for every five large-loop iterations, then $n_{BHC} = 5$.

Figure 5:
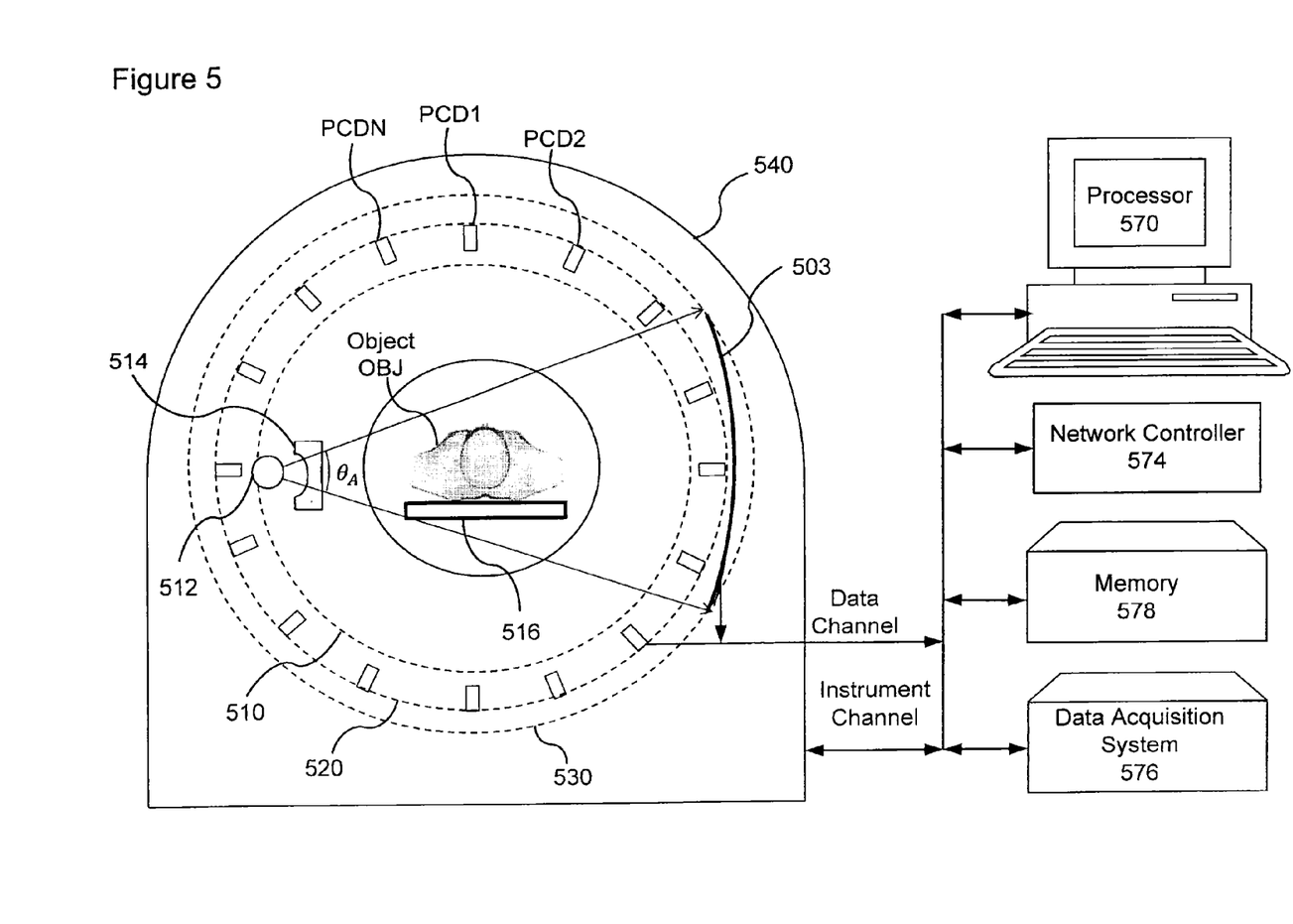
FIG. 5 shows a schematic diagram of an implementation of an image reconstruction apparatus having a coupled-ring topology.
Figure 6:
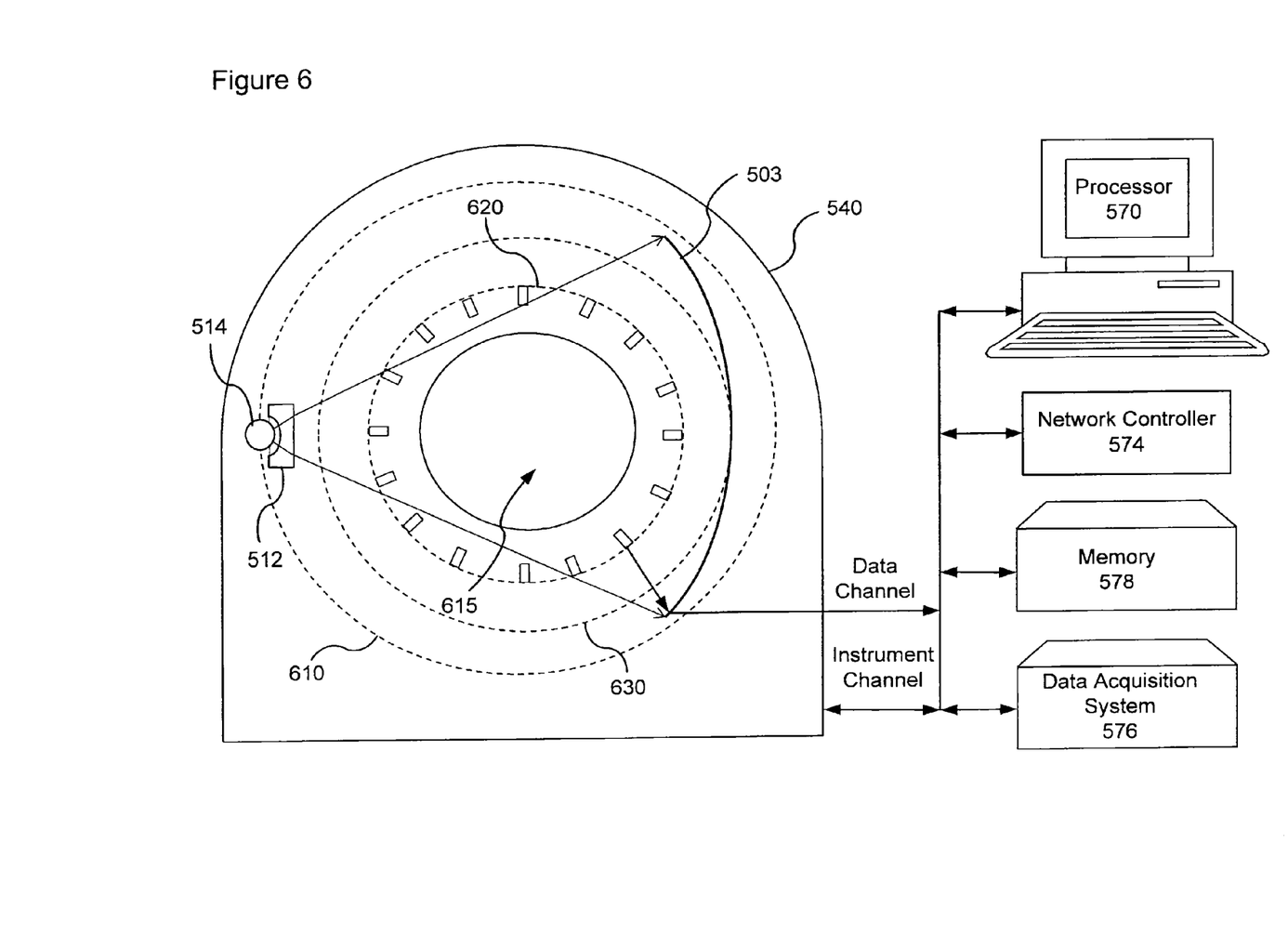
FIG. 6 shows a schematic diagram of an implementation of an image reconstruction apparatus having an inner-ring topology.

FIG. 5 and FIG. 6 show schematic views of CT scanner systems with hybrid systems having energy-integrating detectors arranged in a third-generation geometry and photon-counting detectors (PCDs) arranged in a fourth-generation geometry. FIG. 5 shows a coupled-ring topology with the X-ray source 512 inside the ring of PCDs and the X-ray detector unit 503 outside the ring of PCDs, as discussed in U.S. patent application Ser. No. 13/426,903, incorporated herein by reference in its entirety. In contrast, FIG. 6 shows an inner-ring topology with both the X-ray source 512 and the X-ray detector unit 503 outside the ring of PCDs, as discussed in U.S. patent application Ser. No. 14/092,998, incorporated herein by reference in its entirety.

Illustrated in FIG. 5 is an implementation for placing the PCDs in a predetermined fourth-generation geometry in combination with a detector unit 503 in a predetermined third-generation geometry in a CT scanner system. The diagram illustrates relative positions among an object OBJ to be scanned resting on a table 516, an X-ray source 512, a collimator/filter 514, an X-ray detector 503, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector 503.

Also shown in FIG. 5 is circuitry and hardware for acquiring, storing, processing, and distributing X-ray projection data. The circuitry and hardware include: a processor 570, a network controller 574, a memory 578, and a data acquisition system 576.

In one implementation, the X-ray source 512 and the collimator/filter 514 are fixedly connected to a rotational component 510 that is rotatably connected to a gantry 540. The X-ray detector 503 is similarly fixedly connected to a rotational component 530 that is rotatably connected to the gantry 540. While the PCDs are fixedly connected to a circular component 520 that is fixedly connected to the gantry 540. The gantry 540 houses many pieces of the CT scanner.

The gantry of the CT scanner also includes an open aperture 615 (shown in FIG. 6) enabling the object OBJ that is arranged on a table 516 positioned in a projection plane of the X-rays traveling from the X-ray source to the PCDs and detector unit 503. The "projection plane" is a volume wherein X-rays pass from the X-ray source 512 to the detectors including the PCDs and the detector unit 503. The "object space" is the intersection of the projection plane and the open aperture 615 of the gantry. The "image space" includes the union of projection planes corresponding to all projection angles of the X-ray source 512 as the X-ray source 512 rotates around the aperture of the gantry. The image space is generally larger than the object space enabling image reconstruction for a volume extending beyond the aperture of the gantry and into the structure of the gantry 540.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 5 includes a detector unit 503 having energy-integrating detectors arranged in a conventional third-generation geometry. The detector elements in the detector unit 503 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 520 in a gantry. In one implementation, the photon-counting detectors PCD1 through PCDN are fixedly placed on the circular component 520 at predetermined equidistant positions. In an alternative implementation, the photon-counting detectors PCD1 through PCDN are fixedly placed on the circular component 520 at predetermined non-equidistant positions. The circular component 520 remains stationary with respect to the object OBJ and does not rotate during the data acquisition.

Both the X-ray source 512, collimator 514 (e.g., a bow-tie filter), and the detector unit 503 rotate around the object OBJ while the photon-counting detectors PCD1 through PCDN are stationary with respect to the object OBJ. In one implementation, the X-ray source 512 projects X-ray radiation with a predetermined source fan beam angle $\theta_A$ towards the object OBJ while the X-ray source 512 rotates around the object OBJ outside the sparsely placed photon-counting detectors PCD1 through PCDN. Furthermore, the detector unit 503 is mounted at a diametrically opposed position from the X-ray source 512 across the object OBJ and rotates outside the stationary circular component 520, on which the photon-counting detectors PCD1 through PCDN are fixed in a predetermined sparse arrangement.

In one implementation, the X-ray source 512 optionally travels a helical path relative to the object OBJ, wherein the table 516 moves the object OBJ linearly in a predetermined direction perpendicular to the rotational plane of the rotating portion 510 as the rotating portion 510 rotates the X-ray source 512 and detector unit 503 in the rotational plane.

The motion of the rotating portion 510 around the object OBJ is controlled by a motion control system. The motion control system can be integrated with a data acquisition system or can be separate providing one way information regarding the angular position of the rotating portion 510 and the linear position of the table 516. The motion control system can include position encoders and feedback to control the position of the rotating portion 510 and the table 516. The motion control system can be an open loop system, a closed loop system, or a combination of an open loop system and a closed loop system. The motion control system can use linear and rotary encoders to provide feedback related to the position of the rotating portion 510 and the position of the table 516. The motion control system can use actuators to drive the motion of the rotating portion 510 and the motion of the table 516. These positioners and actuators can include: stepper motors, DC motors, worm drives, belt drives, and other actuators known in the art.

The CT scanner also includes a data channel that routes projection measurement results from the photon counting detectors and the detector unit 503 to a data acquisition system 576, a processor 570, memory 578, network controller 574. The data acquisition system 576 controls the acquisition, digitization, and routing of projection data from the detectors. The data acquisition system 576 also includes radiography control circuitry to control the rotation of the annular rotating frames 510 and 530. In one implementation data acquisition system 576 will also control the movement of the bed 516, the operation of the X-ray source 512, and the operation of the X-ray detectors 503. The data acquisition system 576 can be a centralized system or alternatively it can be a distributed system. In an implementation, the data acquisition system 576 is integrated with the processor 570. The processor 570 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 570 and the data acquisition system 576 can make use of the memory 576 to store, e.g., projection data, reconstructed images, calibration data and parameters, and computer programs.

The processor 570 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 578 can be a hard disk drive, CD-ROM drive, DVD drive, FLASH drive, RAM, ROM or any other electronic storage known in the art.

The network controller 574, such as an Intel Ethernet PRO network interface card from Intel Corporation of America, can interface between the various parts of the CT scanner. Additionally, the network controller 574 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 512 is optionally a single energy source. In another implementation, the X-ray source 512 is configured to perform a kV-switching function for emitting X-ray radiation at a predetermined high-level energy and at a predetermined low-level energy. In still another alternative embodiment, the X-ray source 512 is a single source emitting a broad spectrum of X-ray energies. In still another embodiment, the X-ray source 512 includes multiple X-ray emitters with each emitter being spatially and spectrally distinct.

The detector unit 503 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster response time than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 6 illustrates an inner ring topology for a CT scanner. The primary difference between the CT scanner in FIG. 5 and the CT scanner in FIG. 6 is that in FIG. 6 the X-ray source 512 and the rotational component 610 to which the X-ray source 512 is fixed are outside the circular component 620 to which the PCDs are fixed.

In one implementation, the back surface of each PCD is provided a protective rear cover to shield the PCDs from irradiation from behind as the X-ray source 512 travels outside the first circular component 620 of the sparsely placed photon-counting detectors.

Both the X-ray source 512, collimator 514 (e.g., a bow-tie filter), and the detector unit 503 rotate around the object OBJ in aperture 615 while the photon-counting detectors PCD1 through PCDN are stationary with respect to the object OBJ in aperture 615. In one implementation, the X-ray source 512 and collimator 514 are mounted on the first rotation component 610 mounted in the gantry 540 so that the X-ray source 512 projects X-ray radiation with a predetermined source fan beam angle $\theta_A$ towards the object OBJ while the X-ray source 512 rotates around the object OBJ outside the sparsely placed photon-counting detectors PCD1 through PCDN. Furthermore, the detector unit 503 having energy-integrating detectors arranged in a third-generation geometry is mounted on the second rotation component 630 that is rotatably fixed to the gantry 540. The detector unit 503 is maintained at a position diametrically opposed position from the X-ray source 512 with the object OBJ in the intermediary space between the X-ray source 512 and the detector unit 503—the rotation components 610 and 630 rotating outside the stationary circular component 620, on which the photon-counting detectors PCD1 through PCDN are fixed in a predetermined sparse arrangement.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
   processing circuitry configured to
      obtain projection data representing an intensity of radiation detected at a plurality of detectors, wherein the plurality of detectors includes first detectors and second detectors, the projection data includes a plurality of datasets including a first dataset and a second dataset respectively corresponding to the first detectors and the second detectors, and the first detectors having a different detector configuration than the second detectors, wherein the respective detector configurations of the first detectors and second detectors are respectively determined by a detector type and a projection geometry and of pixel elements arranged within the respective first detectors and second detectors, and
      reconstruct a combined image using the plurality of datasets, wherein each dataset of the plurality of

19 datasets corresponds to a respective system-matrix equation representing respective projection geometries corresponding to the plurality of datasets, and the combined image is reconstructed using system matrices of the plurality of datasets, at least one modified-dual variable, and using a splitting-based subproblem method.

2. The apparatus according to claim 1, wherein the at least one modified-dual variable includes a plurality of modified-dual variables, and the processing circuitry is further configured to reconstruct the combined image using the splitting-based subproblem method, which is a sinogram subproblem method, by updating a plurality of approximate sinograms, each approximate sinogram corresponding to a respective dataset of the projection data, wherein each respective approximate sinogram is calculated to minimize a corresponding sinogram-update expression using a corresponding previous approximate-combined image and a corresponding previous plurality of modified-dual variables, updating an approximate-combined image, wherein the approximate-combined image is calculated to minimize combined-image-update expression using the updated plurality of approximate sinograms and the previous plurality of modified-dual variables, and updating the plurality of modified-dual variables using a plurality of modified-dual-variable-update expressions, wherein each modified-dual-variable-update expression updates the corresponding modified-dual variable using the corresponding previous plurality of modified-dual variables, the corresponding updated approximate sinogram and the updated approximate-combined image.

3. The apparatus according to claim 2, wherein the processing circuitry is further configured to iteratively repeat an update loop, including the steps of updating the plurality of approximate sinograms, updating the approximate-combined image, and updating the plurality of modified-dual variables, until a stopping criteria is satisfied, wherein after each loop iteration, the updated plurality of modified-dual variables become the previous plurality of modified-dual variables, the updated plurality of approximate sinograms become the previous plurality of approximate sinograms, and the updated approximate-combined image becomes the previous approximate-combined image.

4. The apparatus according to claim 3, wherein the processing circuitry is further configured to stop iteratively repeating the update loop when the stopping criteria is satisfied, wherein the stopping criteria is satisfied when either a measure of a difference between the previous approximate-combined image and the updated approximate-combined image is less than a predetermined threshold, or a number of iterations of the update loop reaches a predetermined maximum number of loop iterations.

5. The apparatus according to claim 2, wherein the processing circuitry is further configured to reconstruct the combined image using the sinogram subproblem method, wherein updating the approximate-combined image is performed using a filtered back-projection method to reconstruct a plurality of separate images, each separate image obtained using a system matrix of the corresponding dataset and a difference of the approximate sinogram of the corresponding dataset with the corresponding

20 modified dual variable, and the updated approximate-combined image being a combination of the plurality of separate images.

6. The apparatus according to claim 5, wherein the processing circuitry is further configured to reconstruct the combined image using the sinogram subproblem method, wherein updating the plurality of approximate sinograms further includes that each respective sinogram-update expression includes a first weighted norm of a difference between the corresponding approximate sinogram and a sinogram of the corresponding dataset.

7. The apparatus according to claim 6, wherein the processing circuitry is further configured to reconstruct the combined image using the sinogram subproblem method, wherein updating the plurality of approximate sinograms further includes that a weighting matrix of the first weighted norm of each respective sinogram-update expression is a non-diagonal statistical matrix of the corresponding dataset.

8. The apparatus according to claim 7, wherein the processing circuitry is further configured to reconstruct the combined image using the sinogram subproblem method, wherein updating the plurality of approximate sinograms further includes that each respective sinogram-update expression includes a second weighted norm, an argument of the second weighted norm is a difference among the corresponding approximate sinogram, the corresponding modified-dual variable, and a product of the corresponding system matrix with the previous approximate-combined image, and a weighting matrix of the second weighted norm is a diagonal-weighting matrix, wherein diagonal values of the diagonal-weighting matrix decrease a condition number of the respective sinogram-update expression.

9. The apparatus according to claim 2, wherein the processing circuitry is further configured to reconstruct the combined image using the sinogram subproblem method, wherein updating the approximate-combined image further includes that the combined-image-update expression includes a plurality of weighted norms, an argument of each respective weighted norm is a difference among the corresponding approximate sinogram, a product of the corresponding system matrix with the approximate-combined image, and the corresponding modified-dual variable; and each respective weighted norm in the combined-image-update expression uses a corresponding diagonal-weighting matrix, wherein diagonal values of the diagonal-weighting matrix decrease a condition number of the combined-image-update expression.

10. The apparatus according to claim 9, wherein the processing circuitry is further configured to reconstruct the combined image using the sinogram subproblem method, wherein updating the approximate-combined image further includes that the combined-image-update expression includes a regularization term.

11. The apparatus according to claim 4, wherein the processing circuitry is further configured to reconstruct the combined image using the sinogram subproblem method, wherein a preconditioner is multiplied by arguments of the weighted norms of combined-image-update expression and of the arguments of the weighted norms of the plurality of sinogram-update expressions to increase a convergence rate of the method sinogram subproblem method.

12. The apparatus according to claim 1, wherein the processing circuitry is further configured to reconstruct the combined image using the splitting-based subproblem method that is an image subproblem method, the processing circuitry configured to update a plurality of separate images using a plurality of separate-image-update expressions, each separate image corresponding to a respective dataset of the projection data, wherein each respective separate image is calculated to optimize a corresponding separate-image-update expression using a previous plurality of separate images and a previous at least one modified-dual variable; and update the at least one modified-dual variable using an updated plurality of separate images and the previous at least one modified-dual variable.

13. The apparatus according to claim 12, wherein the processing circuitry is further configured to reconstruct the combined image using the image subproblem method, wherein updating the plurality of separate images is performed using a filtered back-projection method to reconstruct each of the plurality of separate images.

14. The apparatus according to claim 12, wherein the processing circuitry is further configured to reconstruct the combined image using the image subproblem method, wherein updating the plurality of separate images further includes that each of the plurality of separate-image-update expressions includes a weighted norm of a difference between a sinogram of the corresponding dataset and a product of the corresponding system matrix with the separate image of the corresponding dataset.

15. The apparatus according to claim 14, wherein the processing circuitry is further configured to reconstruct the combined image using the image subproblem method, wherein updating the plurality of separate images further includes that a first separate-image-update expression of the plurality of separate-image-update expressions includes a regularization term.

16. The apparatus according to claim 15, wherein the processing circuitry is further configured to reconstruct the combined image using the image subproblem method, wherein updating the plurality of separate images further includes that the plurality of separate-image-update expressions include a norm of a difference among the plurality of separate images and the at least one modified-dual variable.

17. The apparatus according to claim 12, wherein the processing circuitry is further configured to perform a beam-hardening correction on the projection data.

18. The apparatus according to claim 12, wherein the processing circuitry is further configured to iteratively repeat an update loop including the steps of updating a plurality of separate images and updating the at least one modified-dual variable until a stopping criteria is satisfied; and output the combined image, wherein the combined image is a combination of the updated plurality of separate images from a final update loop.

19. A computed tomography imaging apparatus, comprising:

a radiation source configured to provide radiation into an object space;

a plurality of detectors configured to detect radiation exiting the object space;

a rotation component provided around the object space and configured to rotate around the object space, wherein the radiation source is fixedly connected to the rotation component; and processing circuitry configured to obtain projection data representing an intensity of radiation transmitted through the object space and detected at the plurality of detectors, wherein the plurality of detectors includes first detectors and second detectors, the projection data includes a plurality of datasets including a first dataset and a second dataset respectively corresponding to the first detectors and the second detectors, and the first detectors having a different detector configuration thane the second detectors, wherein the respective detector configurations of the first detectors and second detectors are respectively determined by a detector type and a projection geometry and of pixel elements arranged within the respective first detectors and second detectors, and reconstruct the combined image using the plurality of datasets, wherein each dataset of the plurality of datasets corresponds to a respective system-matrix equation representing respective projection geometries corresponding to the plurality of datasets, and the combined image is reconstructed using system matrices of the plurality of datasets at least one modified-dual variable and using a splitting-based subproblem method.

20. A method comprising:

obtaining projection data representing an intensity of radiation transmitted through an object space and detected at a plurality of detectors, wherein the plurality of detectors includes first detectors and second detectors, the projection data includes a plurality of datasets including a first dataset and a second dataset respectively corresponding to the first detectors and the second detectors, and the first detectors having a different detector configuration than the second detector, wherein the respective detector configurations of the first detectors and second detectors are respectively determined by a detector type and a projection geometry and of pixel elements arranged within the respective first detectors and second detectors; and reconstructing the combined image using the plurality of datasets, wherein each dataset of the plurality of datasets corresponds to a respective system-matrix equation representing respective projection geometries corresponding to the plurality of datasets, and the combined image is reconstructed using system matrices of the plurality of datasets, at least one modified-dual variable, and using a splitting-based subproblem method.

* * * * *